US006933138B2

(12) United States Patent
Pyun et al.

(10) Patent No.: US 6,933,138 B2
(45) Date of Patent: Aug. 23, 2005

(54) THERMOSTABLE L-ARABINOSE ISOMERASE AND PROCESS FOR PREPARING D-TAGATOSE

(75) Inventors: Yu Ryang Pyun, Seoul (KR); Byoung Chan Kim, Kyounggi-do (KR); Han Seung Lee, Seoul (KR); Dong Woo Lee, Seoul (KR); Yoon Hee Lee, Seoul (KR)

(73) Assignee: CJ Corp., Seoul (KR)

( * ) Notice: Subject to any disclaimer, the term of this patent is extended or adjusted under 35 U.S.C. 154(b) by 12 days.

(21) Appl. No.: 10/600,689

(22) Filed: Jun. 20, 2003

(65) Prior Publication Data

US 2004/0058419 A1 Mar. 25, 2004

Related U.S. Application Data

(63) Continuation of application No. PCT/KR01/02243, filed on Dec. 22, 2001.

(30) Foreign Application Priority Data

Dec. 22, 2000 (KR) ................................ 10-2000-0080608

(51) Int. Cl.[7] .......................... C12N 15/61; C12N 9/90; C12N 15/63; C12N 1/20; C12P 19/24
(52) U.S. Cl. ...................... 435/94; 435/69.1; 435/320.1; 435/325; 435/252.1; 435/233; 536/23.1
(58) Field of Search ...................... 435/94, 69.1, 320.1, 435/325, 252.1, 233; 536/23.1

(56) References Cited

U.S. PATENT DOCUMENTS

| 5,002,612 A | 3/1991 | Beadle et al. ............... 127/46.1 |
| 6,057,135 A | 5/2000 | Ibrahim et al. ............. 435/105 |
| 2003/0129710 A1 * | 7/2003 | Hansen et al. ............. 435/105 |

OTHER PUBLICATIONS

Nelson et. al. Evidence of lateral gene transfer betwen Archaea and bacteria from genome squence of thrmotoga maritima 399:323–329 (1999).*
Nelson et al. US/09/103,611D Useful genes and Proteins from thermothoga maritima Jun. 24, 1998.*
WO200250282–A1 Kim Pll et. al. Thermostable galactos isomerase protein*
Nelson et. al., "Evidence for lateral gene transfer between archaea and bacteria from genome sequence of Thermotoga maritima." Nature 399:323–329).*
Yoon–Hee Lee et al., *Cloning, Sequencing and Expression of Thermostable L–Arabinose Isomerase from Thermotoga neapolitana*, International Symposium on the Korean Society for Applied Microbiology (2001).
Y. H. Hong et al., *Bioconversion of D–galactose to D–tagatose by Thermostable Immobilized L–arabinose Isomerase from Thermatoga Neapolitana*, The 4th International Congress on Extremophiles (2002).

Sang–Jae Lee et al., *Characterization of Thermostable and Acidiphilic L–arabinose Isomerase from Alicyclobacillus Acidocaldarius*, The 9th International Symposium on the Genetics of Industrial Microorganismx (2002).

Hye–Jung Kim et al., *A Feasible Enzymatic Process for D–tagatose Production by an Immobilized Thermostable L–arabinose Isomerase in a Packed–Bed Bioreactor*, Biotechnol. Prog., 19:400–404 (2003).

Byoung–Chan Kim et al., *Cloning and Expression and Characterization of L–arabinose Isomerase from Thermotoga Neapolitana: Bioconversion of D–galactose to D–tagatose using the Enzyme*, FEMS Microbiology Letters, 212:121–126 (2002).

Pil Kim et al., *Improvement of Tagatose Conversion Rate by Genetic Evolution of Thermostable Galactose Isomerase*, Biotechnol. Appl. Biochem., 34:99–102 (2001).

Pil Kim et al., *High Production of D–tagatose, a Potential Sugar Substitute, using immobilized L–arabinose Isomerase*, Biotechnol. Prog., 17:208–210 (2001).

Miroslav Sedlak and Nancy W.Y. Ho, *Expression of E. coli araBAD Operon Encoding Enzymes for Metabolizing L–arabinose in Saccharomyces cerevisiae*, Enzyme and Microbial Technology, 28:16–24 (2001).

Hoe J. Roh et al., *Bioconversion of D–galactose into D–tagatose by Expression of L–arabinose Isomerase*, Biotechnol. Appl. Biochem., 31:1–4 (2000).

Isabel Sá–Nogueira et al., *The Bacillus subtilis L–arabinose (ara) Operon: Nucleotide Sequence, Genetic Organization and Expression*, Microbiology, 143:957–969 (1997).

Kristine Deanda et al., *Development of an Arabinose–Fermenting Zymomonas mobilis Strain by Metabolic Pathway Engineering*, Applied and Environmental Microbiology, 62:4465–4470 (1996).

Soojay Banerjee et al., *The Evolution of Sugar Isomerases*, Protein Eng., 8:1189–1195 (1995).

* cited by examiner

*Primary Examiner*—Rebecca E. Prouty
*Assistant Examiner*—Kagnew Gebreyesus
(74) *Attorney, Agent, or Firm*—Knobbe, Martens, Olson & Bear LLP.

(57) ABSTRACT

Disclosed are a novel gene coding for L-arabinose isomease derived from *Thermotoga neapolitana* 5068, a thermostable arabinose isomerase expressed from the said gene, a recombinant expression vector containing the said gene, a microorganism transformed with the said expression vector, a process for preparing thermostable arabinose isomerase from the said transformant and a process for preparing D-tagatose employing the said enzyme. Since the recombinant arabinose isomerase is highly thermostable and can produce tagatose with high yield at high temperature, it can be efficiently applied in pharmaceutical and food industries.

15 Claims, 3 Drawing Sheets

Fig. 5

US 6,933,138 B2

THERMOSTABLE L-ARABINOSE ISOMERASE AND PROCESS FOR PREPARING D-TAGATOSE

RELATED APPLICATIONS

This application is a continuing application under 35 U.S.C. §365(c) claiming the benefit of the filing date of PCT Application No. PCT/KR01/02243 designating the United States, filed Dec. 22, 2001. The PCT Application was published in English as WO 02/052021 A1 on Jul. 4, 2002, and claims the benefit of the earlier filing date of Korean Patent Application Nos. 2000/80608, filed Dec. 22, 2000, and 2001/80711, filed Dec. 18, 2001. The contents of Korean Patent Application Nos. 2000/80608 and 2001/80711, and the international application No. PCT/KR01/02243 and the publication 02/052021 A1 are incorporated herein by reference in their entirety.

BACKGROUND OF THE INVENTION

1. Field of the Invention

The present invention relates generally to production of an enzyme for use in production of a sweetener. More particularly, the present invention relates to production of arabinose isomerase and tagatose.

2. Description of the Related Art

In recent years, growing concerns about health have led much research effort to the development of healthful foods. As one of the above efforts, sugar alcohols have been proposed as sweeteners which can substitute sugar, known to cause adult diseases, and are practically being used. Since the said sweeteners are known to have adverse side effects such as causing diarrhea when ingested more than certain amount, there is an urgent need to develop substitutional sweeteners without harmful effects.

Among substitutional sweeteners which have little side effect, tagatose, a keto-sugar of galactose, has similar sweetness to D-fructose, and has known not to be absorbed or metabolized in the body, making tagatose a safe low-caloric substitutional sweetener for sugar. Also, it has been reported that tagatose can be employed as an intermediate for the preparation of useful optically active isomers, detergents and cosmetics, also, as an additive or raw material for the synthesis of drugs, especially, its ability to lower blood sugar level renders tagatose a therapeutic and preventive agent for diabetes, and a low caloric diet agent.

Currently, tagatose is mostly prepared via chemical synthesis from galactose (see: U.S. Pat. No. 5,002,612), which comprises the steps of isomerization of galactose catalyzed by metal hydroxide in the presence of inorganic salts to form an intermediate of metal hydroxide-tagatose complex, and neutralization of the complex by adding acid to yield final product, tagatose.

Alternative method for manufacturing tagatose is an enzymatic method in which galactose is converted into tagatose via conversion of aldose or aldose derivatives into ketose or ketose derivatives. Especially, it has been reported that arabinose isomerase which catalyzes the conversion reaction of L-arabinose into L-ribulose can be employed for production of tagatose in vitro using galactose as a substrate. However, the yield of tagatose produced by arabinose isomerase from galactose is as low as 20%, hindering industrial application of conversion process of galactose into tagarose. Although the method for manufacturing tagatose from milk or cheese has been developed (see: U.S. Pat. No. 6,057,135), again, low yield is the limitation for its industrial use.

Under the circumstances, there are strong reasons for exploring and developing a novel enzyme which can produce tagatose with high yield.

SUMMARY OF THE INVENTION

An aspect of the present invention provides an isolated polynucleotide coding for an arabinose isomerase from *Thermotoga neapolitana*. The isolated polynucleotide has the sequence of SEQ. ID NO: 3.

Another aspect of the present invention provides an expression vector, which comprises the above-described isolated polynucleotide. The expression vector is pTNAI.

Another aspect of the present invention provides a host cell transformed with the above-described expression vector. The host cell is *E. coli*. The host cell is *E. coli* BL21/DE3 (pTNAI) deposited as Accession No. KCCM-10231.

Another aspect of the present invention provides an isolated polypeptide of arabinose isomerase isolated from *Thermotoga neapolitana*.

Still another aspect of the present invention provides an isolated polypeptide of arabinose isomerase encoded by the above-described polynucleotide. The arabinose isomerase has the amino acid sequence of SEQ. ID NO: 4. The isolated polypeptide further comprises a solid support. The solid support is a silica bead.

Still another aspect of the present invention provides a method of producing an arabinose isomerase. The method comprises: providing the above-described host cell; and culturing the host cell in a medium, thereby producing an arabinose isomerase. The method further comprises purifying or isolating the arabinose isomerase. The host cell is *E. coli* BL21/DE3 (pTNAI) deposited as Accession No. KCCM-10231.

Still another aspect of the present invention is an arabinose isomerase produced by the above-described method.

A still further aspect of the present invention provides a method of producing tagatose. The method comprises: providing the above-described isolated polypeptide; and admixing the arabinose isomerase with galactose, thereby causing a reaction and producing tagatose. The reaction is carried out at a pH from about 5 to about 8. The reaction is carried out at a temperature from about 50° C. to about 100° C. The reaction is carried out at a temperature from about 70° C. to about 95° C. The method of claim 17, wherein the isolated polypeptide is attached to a solid support. The solid support is a silica bead. The reaction is carried out at a temperature of about 80° C.

BRIEF DESCRIPTION OF THE DRAWINGS

The above and the other objects and features of the present invention will become apparent from the following descriptions given in conjunction with the accompanying drawings.

DETAILED DESCRIPTION OF EMBODIMENTS

The present inventors have made an effort to develop an enzyme which can produce tagatose with high yield, and have found that tagatose can be produced with high yield from galactose by employing a recombinant arabinose isomerase produced from *E. coli* transformed with recombinant vector containing arabinose isomerase gene derived from *Thermotoga neapolitana* 5068.

To prepare thermophilic or thermostable arabinose isomerase for industrial use, the present inventors have cloned a gene coding for arabinose isomerase from genomic DNA of *Thermotoga neapolitana* 5068 (DSM 5608) and analyzed nucleotide sequence and deduced amino acid sequence from the said gene. The nucleotide sequence and deduced amino acid sequence of the gene encoding arabinose isomerase of an embodiment of the present invention (SEQ ID NO: 3) has shown to have 83.2% and 94.8% homology, respectively, to those of the putative arabinose isomerase gene of *Thermotoga maritima* of which entire nucleotide sequence has been verified via genome project.

For high level expression of the said cloned arabinose isomerase in *E. coli*, the gene coding for the enzyme was inserted into an expression vector pET22b(+) (Novagen, U.S.A.) to construct a recombinant expression vector pTNAI, which was then introduced into *E. coli* BL21. The transformed recombinant *E. coli* was named "*E. coli* BL21/DE3 (pTNAI)" and deposited with an international depository authority, the Korean Culture Center of Microorganisms (KCCM, #361-221 Hongje-1-dong, Seodaemun-gu, Seoul, Republic of Korea) on Dec. 4, 2000 as accession no. KCCM-10231.

The said *E. coli* BL21/DE3 (pTNAI) was grown to obtain recombinant arabinose isomerase, which was characterized to have optimum pH of 7.0, optimum reaction temperature of 85° C. Furthermore, over 80% of remaining activity was measured after 2 hour heat treatment at 80° C., indicating that the enzyme is exceedingly heat stable.

Tagatose can be produced by employing arabinose isomerase of the embodiment of the present invention prepared from *E. coli* transformed with a recombinant expression vector containing the gene for arabinose isomerase derived from *Thermotoga* sp., and galactose as a substrate, under a condition of pH 5 to 8, more preferably pH 6 to 8, most preferably pH 7, and 60 to 100° C., more preferably 70 to 95° C., most preferably 85° C.

Aqueous solution of galactose was subjected to isomerization reaction employing recombinant arabinose isomerase of the embodiment of the present invention, and it has been found that conversion rate into tagatose was over 68% at 80° C.

When the said recombinant arabinose isomerase is employed for industrial production of tagatose, soluble form of the enzyme may be employed, nevertheless, it is more preferable to immobilize the enzyme on the beads used in industry. For example, in case of the recombinant arabinose isomerase of the embodiment of the present invention immobilized on silica beads, the remaining activity was measured to be over 80% of original activity after 20 day-heat treatment at 90° C., thus, it can be applied for thermal process over 80° C. in industry.

EXAMPLES

Embodiments of the present invention are further illustrated in the following examples, which should not be taken to limit the scope of the invention.

Example 1

Cloning of Arabinose Isomerase Gene

*Thermotoga neapolitana* 5068 (DSM 5068) was grown under an anaerobic condition and cells were harvested by centrifugation at 8000×g for 10 minutes. Genomic DNA isolated from the cells harvested above was partial digested with Sau3AI (TaKaRa Biotechnology, Japan) to obtain 12 kb or shorter fragments of DNA. The DNA fragments were inserted into ZAP Expression Vector (Stratagene, U.S.A.) and packaged to prepare a genomic library of *Thermotoga neapolitana* 5068. Nucleotide sequences of the genes for conventional thermophilic or thermostable arabinose isomerase were analyzed to prepare primer araAF: 5'-ATGATCGATCTCAAACAGTATGAG-3' (SEQ ID NO: 1) and primer araAR: 5'-TCATCTTTTTAAAAGTCCCC-3' (SEQ ID NO: 2), which were used in PCR for the preparation of probes for DNA-DNA hybridization. The genomic library prepared above was screened for DNA fragments containing arabinose isomerase gene by DNA-DNA hybridization to obtain a recombinant vector containing a gene encoding arabinose isomerase of *Thermotoga neapolitana* 5068. The nucleotide sequence of arabinose isomerase gene (SEQ ID No: 3) cloned above and the deduced amino acid sequence (SEQ ID No: 4) from the said gene were compared with those of known arabinose isomerase genes, respectively (see: Table 1).

TABLE 1

Comparison of homology between arabinose isomerase of one embodiment of the present invention and known arabinose isomerases

| Strain | Gene Sequence (homology, %) | Amino Acid Sequence (homology, %) |
| --- | --- | --- |
| *Thermotoga maritima* | 83.2 | 94.8 |
| *Bacillus stearothermophilus* | 61.9 | 62.8 |
| *Bacillus halodurans* | 59.1 | 59.0 |
| *Bacillus subtilis* | 58.6 | 55.5 |
| *Salmonella typhimurium* | 57.8 | 54.5 |
| *Escherichia coli* | 59.0 | 54.3 |
| *Mycobacterium smegmatis* | 56.3 | 50.7 |

As shown in Table 1, it has been found that the arabinose isomerase of the embodiment of the present invention is a novel enzyme which has 83.2% homology of nucleotide sequence and 94.8% homology of amino acid sequence to the sequences of published putative arabinose isomerase of *Thermotoga maritima*, respectvely.

Example 2

Preparation of Recombinant Expression Vector and Recombinant *E. coli*

Figure 1:
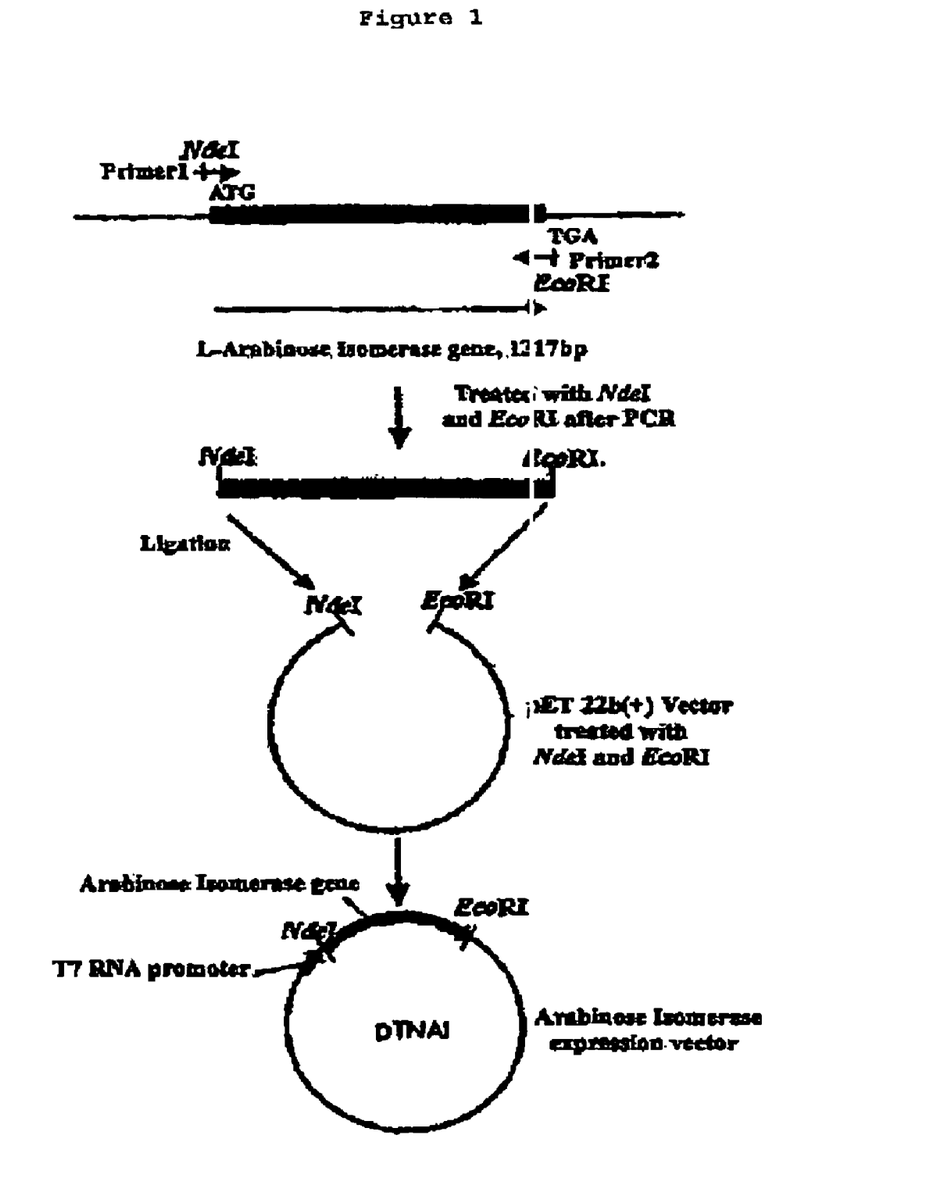
FIG. 1 is a schematic diagram showing the construction strategy of an expression vector containing arabinose isomerase gene of the invention.

In order to obtain high level expression of the said thermostable arabinose isomerase in *E. coli* using the arabinose isomerase gene obtained in Example 1, the said gene was inserted into an expression vector pET 22b(+) (Novagen, U.S.A.) double-digested with NdeI and EcoRI to construct a recombinant expression vector pTNAI (see: FIG. 1), which was then introduced into *E. coli* BL21. The transformed recombinant *E. coli* was named "*E. coli* BL21/DE3 (pTNAI)" and deposited with an international depository authority, the Korean Culture Center of Microorganisms (KCCM, #361-221 Hongje-1-dong, Seodaemun-gu, Seoul, Republic of Korea) on Dec. 4, 2000 as accession no. KCCM-10231.

Example 3

Expression of Recombinant Arabinose Isomerase

The recombinant *E. coli* BL21/DE3 (pTNAI) (KCCM-10231) prepared in Example 2 was inoculated into LB (Luria-Bertani) medium (1% v/v) and incubated at 37° C. for 2 hours, to which lactose was added to a final concentration of 1 mM and expression of recombinant arabinose isomerase was induced for 12 hours. For assay of expressed arabinose isomerase, cells were collected by centrifugation at 8000×g for 10 minutes, resuspended in 10 ml of 100 mM MOPS buffer (4-morpholinepropanesulfonic acid, pH 7.0), and then disrupted by sonication to obtain crude enzyme, with which galactose isomerization reaction was carried out. Galactose isomerization was performed by mixing 100 µl of the said crude enzyme solution with 40 mM (final concentration) galactose as a substrate, followed by adding 1 ml of enzyme reaction buffer (100 mM MOPS buffer, pH 7.0) containing cofactors (1 mM $MnCl_2$, 1 mM $CoCl_2$) and incubating at 85° C. for 20 minutes. The product of the above reaction was detected using cysteine-carbazole-sulfuric acid method (see: Dische, Z., and E. Borenfreund., A New Spectrophotometric Method for the Detection and Determination of Keto Sugars and Trioses, *J. Biol. Chem.*, 192:583–587, 1951), and it has been found that normal galactose isomerization has been undergone.

Example 4

Purification of Recombinant Arabinose Isomerase

For purification of recombinant arabinose isomerase expressed by the method described in Example 3, cells were collected by centrifugation at 8000×g for 19 minutes and cell wall of *E. coli* was disrupted by sonication, which was followed by centrifugation at 20,000×g for 20 minutes to obtain supernatant. Then, the said supernatant was heat-treated at 85° C. for 20 minutes, centrifuged at 20,000×g for 20 minutes to get rid of precipitate, and the supernatant was further purified by ammonium sulfate-mediated precipitation and finally ion-exchange column chromatography (Q-Sepharose Fast Flow, Pharmacia, Sweden). pH dependancy of the said purified enzyme was analyzed and optimum pH was found to be around 7.0.

Example 5

Optimum pH and Optimum Temperature of Recombinant Arabinose Isomerase

Figure 2:
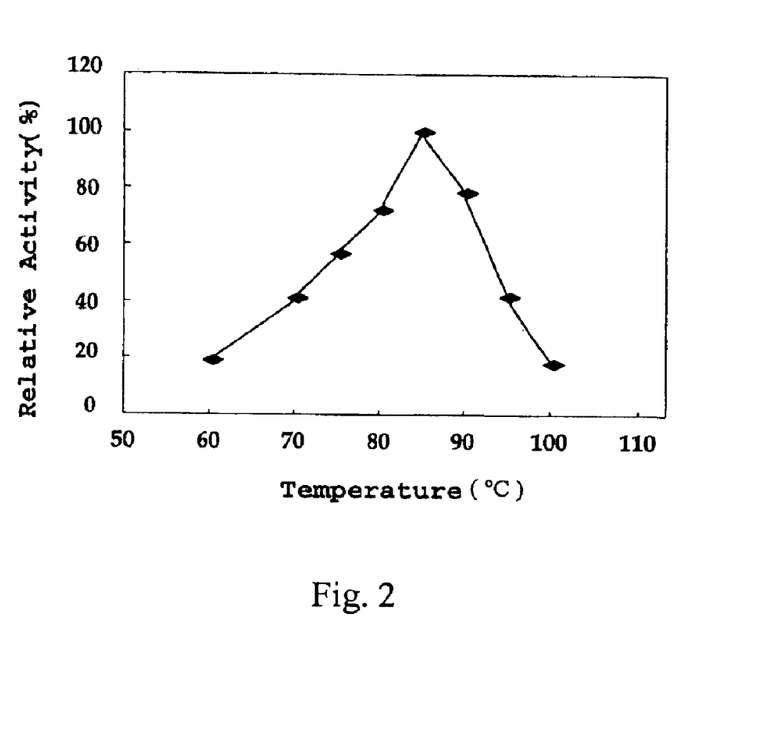
FIG. 2 is a graph showing activity profile of arabinose isomerase of the invention depending on temperature.

Activity of the purified recombinant arabinose isomerase prepared in Example 4 was analyzed on galactose substrate and optimum pH was found to be around 7.0. Optimum temperature for isomerization reaction was determined using the same method as described in Example 3. The tested reaction temperatures for galactose isomerization were 60, 70, 75, 80, 85, 90 and 100° C., and maximum activity was obtained around 85° C. (see: FIG. 2).

Example 6

Thermostability of Recombinant Arabinose Isomerase

Figure 3:
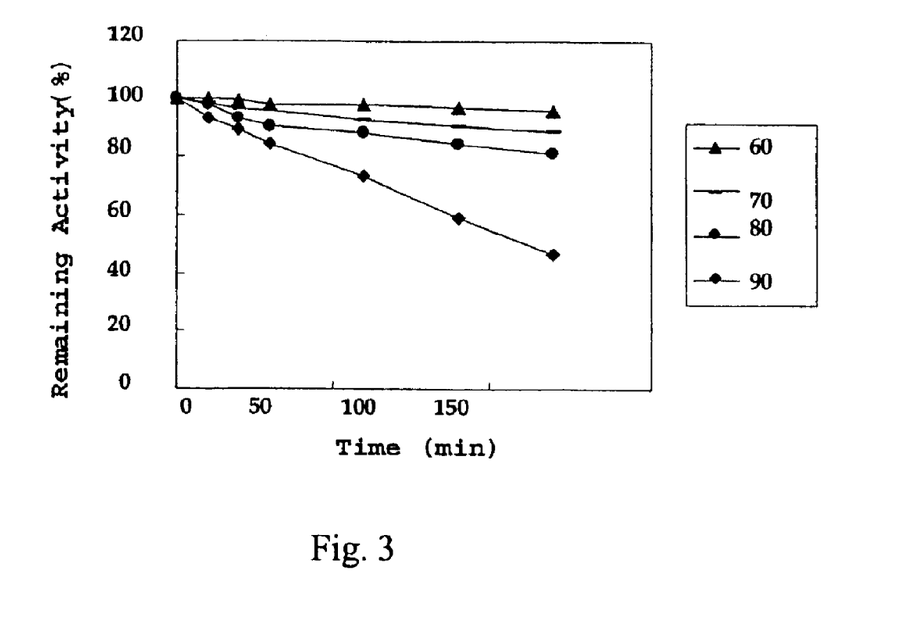
FIG. 3 is a graph showing thermostability of arabinose isomerase of the invention.

To assess the thermostability of recombinant arabinose isomerase of the embodiment of the present invention, crude enzyme prepared in Example 3 was heat-treated at 60, 70, 80 and 90° C. for 10, 20, 30, 60, 90 and 120 minutes respectively, and remaining activity of recombinant arabinose isomerase for isomerization was determined as described in Example 3 (see: FIG. 3). As shown in FIG. 3, it has been found that over 80% of enzyme activity was remained after 2 hour heat-treatment at 80° C.

Example 7

Conversion Rate of Galactose into Tagatose at Various Temperature

By employing recombinant arabinose isomerase of the embodiment of the present invention, the conversion rate of galactose into tagatose was determined at various temperatures and various time points. Substrate used was 10 mM galactose instead of 40 mM galactose in enzyme reaction mixture in Example 3. After incubation at 60, 70, 80 and 90° C. for 20 hours, tagatose yield was determined employing BioLC (see: Table 2 and FIG. 4).

TABLE 2

| Conversion rate of galactose into tagatose at various temperature | | | | |
|---|---|---|---|---|
| Enzyme Reaction Temperature | 60° C. | 70° C. | 80° C. | 90° C. |
| Conversion Rate into Tagatose | 31.7 | 40.4 | 68.1 | 57.4 |

Figure 4:
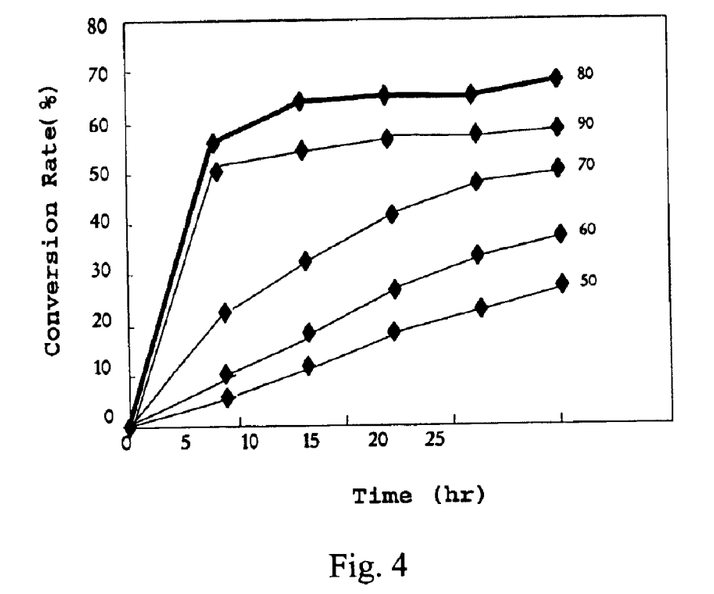
FIG. 4 is a graph showing the time course of conversion rate of galactose into tagatose by arabinose isomerase of the invention at various reaction temperatures.

As shown in Table 2 and FIG. 4, the higher the reaction temperature was, the higher tagatose yield was obtained, and conversion rate into tagatose was as high as 68% at 80° C.

Example 8

Immobilization of Arabinose Isomerase and Improvement of Thermostability

Figure 5:
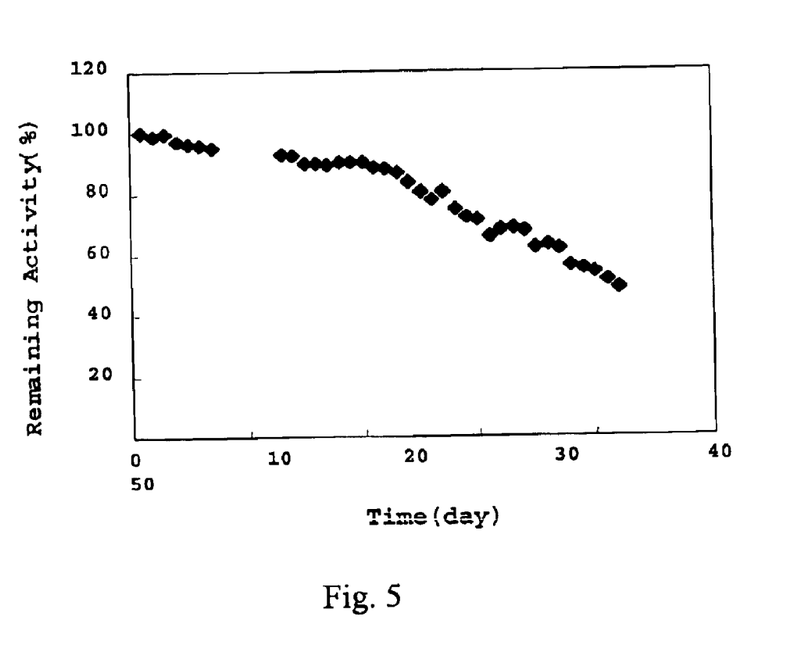
FIG. 5 is a graph showing the time course of changes in thermostability of immobilized arabinose isomerase of the invention.

Arabinose isomerase was immobilized on silica beads, heat-treated under an aqueous condition at 90° C. and the remaining activity was determined at various time points (see: FIG. 5). As shown in FIG. 5, remaining activity of the immobilized enzyme was over 80% after 20 day-heat treatment at 90° C. and over 60% after 30 day-heat treatment, indicating that the immobilized arabinose isomerase of the embodiment of the present invention can be applied for thermal process in industry.

As clearly illustrated and demonstrated above, the present invention provides, among other things, a novel gene coding for L-arabinose isomease derived from *Thermotoga neapolitana* 5068, a thermostable arabinose isomerase expressed from the said gene, a recombinant expression vector containing the said gene, a microorganism transformed with the said expression vector, a process for preparing thermostable arabinose isomerase from the said transformant and a process for preparing D-tagatose employing the said enzyme. Since the recombinant arabinose isomerase of the embodiment of the present invention is highly thermostable and can produce tagatose with high yield at high temperature, it can be efficiently applied in pharmaceutical and food industries.

Indications Relating To Deposited Microorganism or other Biological Material (PCT Rule 13bis)

A. The indications made below relate to the deposited microorganism or other biological material referred to in description B. IDENTIFICATION OF DEPOSIT             Further deposits
                                          are identified on
Name of depositary institution
Korean Culture Center of Microorganisms (KCCM)
Address of depositary institution (including postal code and country)
Korean Culture Center of Microorganisms (KCCM)

-continued 361-221, Yurim B/D, Hongje-1-dong, Seodaemun-gu
Seoul, 120-091, Republic of Korea
Date of deposit                                Accession
Dec. 04, 2000                                  Number
                                               KCCM-10231
C. ADDITIONAL INDICATIONS (leave blank if not applicable) This
information continues on an additional sheet ☐

-continued

D. DESIGNATED STATES FOR WHICH INDICATIONS ARE MADE
(if the indications are not for all designated States)
E. SEPARATE FURNISHING OF INDICATIONS (leave blank if not applicable)
The indications listed below will be submitted to the International Bureau later (specify the general nature of the indications
e.g., "Accession Number of Deposit")

What is claimed is:

1. An isolated arabinose isomerase polypeptide comprising SEQ ID NO: 4 encoded by a polynucleotide from *Thermotoga neapolitana*.

2. The isolated polypeptide of claim 1, wherein said polypeptide is attached to a solid support.

3. The isolated polypeptide of claim 2, wherein the solid support is a silica bead.

4. An arabinose isomerase produced by a method comprising:
   providing a host cell transformed with the polynucleotide sequence SEQ ID NO: 3 from *Thermotoga neapolitana;* and
   culturing the host cell in a medium, thereby producing an arabinose isomerase.

5. A method of producing tagatose, comprising:
   providing the isolated polypeptide of claim 1; and
   admixing the arabinose isomerase with galactose, thereby causing a reaction and producing tagtose.

6. The method of claim 5, wherein the reaction is carried out at a pH from about 5 to bout 8.

7. The method of claim 5, wherein the reaction is carried out at a temperature from about 50° C. to about 100° C.

8. The method of claim 7, wherein the reaction is carried out at a temperature from about 70° C. to about 95° C.

9. The method of claim 5, wherein the isolated polypeptide is attached to a solid support.

10. The method of claim 9, wherein the solid support is a silica bead.

11. The method of claim 5, wherein the reaction is carried out at a temperature of about 80° C.

12. The isolated polypeptide of claim 1, wherein the polynucleotide has the sequence of SEQ. ID NO: 3.

13. The arabinose isomerase of claim 4, wherein the arabinose isomerase has the amino acid sequence of SEQ. ID NO: 4.

14. The arabinose isomerase of claim 4, wherein the host cell is *E. coli*.

15. The arabinose isomerase of claim 4, wherein the host cell is *E. coli* BL21/DE3 (pTNAI) deposited as Accession No. KCCM-10231.

* * * * *

UNITED STATES PATENT AND TRADEMARK OFFICE
CERTIFICATE OF CORRECTION

PATENT NO. : 6,933,138 B2  
APPLICATION NO. : 10/600689  
DATED : August 23, 2005  
INVENTOR(S) : Pyun et al.

Page 1 of 2

It is certified that error appears in the above-identified patent and that said Letters Patent is hereby corrected as shown below:

On the title page, item [56]:
    At column 1, line 1 under "Other Publications," please delete "et. al." and insert -- et al. --,therefor.

On the title page, item [56]:
    At column 1, line 1 under "Other Publications," please delete "betwen" and insert -- between -- therefor.

On the title page, item [56]:
    At column 1, line 2 under "Other Publications," please delete "squence" and insert -- sequence -- therefor.

On the title page, item [56]:
    At column 1, line 2 under "Other Publications," please delete "thrmotoga" and insert -- thermotoga -- therefor.

On the title page, item [56]:
    At column 1, line 5 under "Other Publications," please delete "thermothoga" and insert -- thermotoga -- therefor.

On the title page, item [56]:
    At column 1, line 6 under "Other Publications," please delete "et. al." and insert -- et al. -- therefor.

On the title page, item [56]:
    At column 1, line 7 under "Other Publications," please insert -- . -- after "protein".

On the title page, item [56]:
    At column 1, line 8 under "Other Publications," please delete "et. al.," and insert -- et al., -- therefor.

At column 4, line 49, please delete "respectvely" and insert -- respectively -- therefor.

At column 11, line 61, in Claim 5, please delete "tagtose" and insert -- tagatose -- therefor.

UNITED STATES PATENT AND TRADEMARK OFFICE
CERTIFICATE OF CORRECTION

PATENT NO. : 6,933,138 B2
APPLICATION NO. : 10/600689
DATED : August 23, 2005
INVENTOR(S) : Pyun et al.

It is certified that error appears in the above-identified patent and that said Letters Patent is hereby corrected as shown below:

At column 11, line 63, in Claim 6, please delete "bout" and insert -- about -- therefor.

Signed and Sealed this

Seventh Day of August, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: primer araAF

<400> SEQUENCE: 1
atgatcgatc tcaaacagta tgag                                      24

<210> SEQ ID NO 2
<211> LENGTH: 20
<212> TYPE: DNA
<213> ORGANISM: Artificial Sequence
<220> FEATURE:
<223> OTHER INFORMATION: primer araAR

<400> SEQUENCE: 2
tcatcttttt aaaagtcccc                                           20

<210> SEQ ID NO 3
<211> LENGTH: 1491
<212> TYPE: DNA
<213> ORGANISM: Thermotoga neapolitana 5068

<400> SEQUENCE: 3
atgatcgatc tcaaacagta tgagttctgg tttcttgtcg gcagccagta tctctacggt      60
ctggagacgt tgaagaaggt agagcagcag gcaagcagga tagttgaggc actgaacaat     120
gatcccattt ttccctcaaa gatcgttctg aaacctgttc tgaaaaattc cgccgagatc     180
agagagatct tcgaaaaggc aaatgcagaa ccaaaatgcg ccggtgtcat cgtgtggatg     240
cacacgttct caccttcgaa gatgtggata agaggcctct ccatcaataa aaaacccctg     300
cttcacctcc acacccagta caacagggag atcccgtggg acacgatcga tatggactac     360
atgaacctga accaatctgc ccacggtgac agggaacacg gattcattca cgcgaggatg     420
agactcccaa gaaaggtcgt ggtgggacat tgggaagaca gagaagtcag ggaaaagatc     480
gcaaaatgga tgagagtggc ctgcgcgata caggatggaa gaactggaca gatcgtgaga     540
ttcggcgata acatgagaga ggttgccagc accgaagacg acaaggtgga ggcacagata     600
aaactcggct ggtccataaa cacctggggt gtcggagagc tcgccgaggg agtgaaggcg     660
gttccagaaa acgaagtgga ggaattgttg aaggagtaca agaaaggta catcatgcca     720 gaagacgaat acagcctcaa agcgatcaga gaacaggcga agatggagat tgcactgaga     780

-continued

```
gagtttctga aagagaagaa tgccatcgcc ttcaccacca ccttcgagga tcttcacgat    840
cttccccagc ttcccggtct tgcagtccag aggctcatgg aggaagggta tggatttgga    900
gcggaaggag actggaaggc agccgggctt gtgagggctt tgaaggtcat gggagctggt    960
cttcccggtg gtacatcctt catggaggac tacacctacc atctcacacc gggaaacgaa   1020
ctcgtgctgg gagcgcacat gctagaggtg tgccccacga tcgctaagga aaagccaaga   1080
atagaggtgc atcctctcag catcggtgga aaagcagatc ctgcacgcct tgttttcgat   1140
ggacaagaag gtcccgctgt caacgcctcc atcgttgaca tgggaaacag gttcaggctg   1200
gtagtgaaca gagtgttgtc tgttcccatt gaaaggaaga tgcccaaact tccaacggca   1260
agagttttgt ggaagccgct tcctgatttc aagagggcga cgactgcgtg gattctcgct   1320
ggaggatccc atcatactgc cttctcaaca gcggtggatg tggagtacct catcgactgg   1380
gcggaggctt tggagataga gtatcttgtc atcgatgaaa atctggatct ggagaacttc   1440
aaaaaggaac tgagatggaa cgaactctac tggggacttt taaaaagatg a            1491
```

<210> SEQ ID NO 4
<211> LENGTH: 496
<212> TYPE: PRT
<213> ORGANISM: Thermotoga neapolitana 5068

<400> SEQUENCE: 4

```
Met Ile Asp Leu Lys Gln Tyr Glu Phe Trp Phe Leu Val Gly Ser Gln
  1               5                  10                  15

Tyr Leu Tyr Gly Leu Glu Thr Leu Lys Lys Val Glu Gln Gln Ala Ser
             20                  25                  30

Arg Ile Val Glu Ala Leu Asn Asn Asp Pro Ile Phe Pro Ser Lys Ile
         35                  40                  45

Val Leu Lys Pro Val Leu Lys Asn Ser Ala Glu Ile Arg Glu Ile Phe
     50                  55                  60

Glu Lys Ala Asn Ala Glu Pro Lys Cys Ala Gly Val Ile Val Trp Met
 65                  70                  75                  80

His Thr Phe Ser Pro Ser Lys Met Trp Ile Arg Gly Leu Ser Ile Asn
                 85                  90                  95

Lys Lys Pro Leu Leu His Leu His Thr Gln Tyr Asn Arg Glu Ile Pro
            100                 105                 110

Trp Asp Thr Ile Asp Met Asp Tyr Met Asn Leu Asn Gln Ser Ala His
        115                 120                 125

Gly Asp Arg Glu His Gly Phe Ile His Ala Arg Met Arg Leu Pro Arg
    130                 135                 140

Lys Val Val Gly His Trp Glu Asp Arg Glu Val Arg Glu Lys Ile
145                 150                 155                 160

Ala Lys Trp Met Arg Val Ala Cys Ala Ile Gln Asp Gly Arg Thr Gly
                165                 170                 175

Gln Ile Val Arg Phe Gly Asp Asn Met Arg Glu Val Ala Ser Thr Glu
            180                 185                 190

Asp Asp Lys Val Glu Ala Gln Ile Lys Leu Gly Trp Ser Ile Asn Thr
        195                 200                 205

Trp Gly Val Gly Glu Leu Ala Glu Gly Val Lys Ala Val Pro Glu Asn
    210                 215                 220

Glu Val Glu Glu Leu Leu Lys Glu Tyr Lys Glu Arg Tyr Ile Met Pro
225                 230                 235                 240

Glu Asp Glu Tyr Ser Leu Lys Ala Ile Arg Glu Gln Ala Lys Met Glu
                245                 250                 255
```

-continued

```
Ile Ala Leu Arg Glu Phe Leu Lys Glu Lys Asn Ala Ile Ala Phe Thr
            260                 265                 270

Thr Thr Phe Glu Asp Leu His Asp Leu Pro Gln Leu Pro Gly Leu Ala
        275                 280                 285

Val Gln Arg Leu Met Glu Glu Gly Tyr Gly Phe Gly Ala Glu Gly Asp
    290                 295                 300

Trp Lys Ala Ala Gly Leu Val Arg Ala Leu Lys Val Met Gly Ala Gly
305                 310                 315                 320

Leu Pro Gly Gly Thr Ser Phe Met Glu Asp Tyr Thr Tyr His Leu Thr
                325                 330                 335

Pro Gly Asn Glu Leu Val Leu Gly Ala His Met Leu Glu Val Cys Pro
            340                 345                 350

Thr Ile Ala Lys Glu Lys Pro Arg Ile Glu Val His Pro Leu Ser Ile
            355                 360                 365

Gly Gly Lys Ala Asp Pro Ala Arg Leu Val Phe Asp Gly Gln Glu Gly
        370                 375                 380

Pro Ala Val Asn Ala Ser Ile Val Asp Met Gly Asn Arg Phe Arg Leu
385                 390                 395                 400

Val Val Asn Arg Val Leu Ser Val Pro Ile Glu Arg Lys Met Pro Lys
            405                 410                 415

Leu Pro Thr Ala Arg Val Leu Trp Lys Pro Leu Pro Asp Phe Lys Arg
            420                 425                 430

Ala Thr Thr Ala Trp Ile Leu Ala Gly Gly Ser His His Thr Ala Phe
            435                 440                 445

Ser Thr Ala Val Asp Val Glu Tyr Leu Ile Asp Trp Ala Glu Ala Leu
    450                 455                 460

Glu Ile Glu Tyr Leu Val Ile Asp Glu Asn Leu Asp Leu Glu Asn Phe
465                 470                 475                 480

Lys Lys Glu Leu Arg Trp Asn Glu Leu Tyr Trp Gly Leu Leu Lys Arg
                485                 490                 495
```